United States Patent [19]

Braiman

[11] Patent Number: 5,719,195
[45] Date of Patent: Feb. 17, 1998

[54] TREATMENT OF PSORIASIS WITH 11-CIS-RETINOIC ACID

[75] Inventor: Mark S. Braiman, Charlottesville, Va.

[73] Assignee: 4 Thought Technologies, Charlottesville, Va.

[21] Appl. No.: 435,804

[22] Filed: May 5, 1995

[51] Int. Cl.$^6$ .................................................. A61K 1/04
[52] U.S. Cl. .................................................. 514/725
[58] Field of Search .................................................. 514/725

[56] References Cited

U.S. PATENT DOCUMENTS 5,093,360  3/1992  Yu et al. .................................................. 514/463

Primary Examiner—Zohreh Fay
Attorney, Agent, or Firm—Sheldon H. Parker

[57] ABSTRACT

A particular uncommon isomer of retinoic acid (namely 11-cis-retinoic acid, or neotretinoin) is useful in treating conditions involving abnormal cellular differentiation and hyperproliferation, such as psoriasis. A new method of synthesizing this isomer, in quantities that has allowed it to be compared therapeutically with the more commonly available all-trans and 13-cis isomers, is presented. As measured on the inventor's own psoriasis-affected skin, topical treatment with 11-cis-retinoic acid is much more efficacious in reducing symptoms and has substantially reduced side effects, as compared to topical treatment with the other isomers. A single application of a 0.001% neotretinoin cream to psoriasis lesions leads within 48 hours to substantial amelioration of associated dermatological symptoms, including itching, scaling, bleeding, and abnormal appearance. Continued application leads to complete remission, and replacement of lesions by skin that is indistinguishable from surrounding healthy tissue, without any noticeable irritation, erythema, or other problematic side effects. A less efficacious but more easily-implemented version of the same invention employs ultraviolet or blue-light irradiation of a commercially-available gel containing tretinoin as a means of effecting partial conversion of the tretinoin to neotretinoin, prior to application of the gel to psoriasis-affected areas of skin.

14 Claims, No Drawings

TREATMENT OF PSORIASIS WITH 11-CIS-RETINOIC ACID

FIELD OF THE INVENTION

The invention relates to methods using retinoids to treat conditions involving hyperproliferation and incomplete differentiation of cells, particularly skin conditions such as psoriasis.

BACKGROUND OF THE INVENTION

Differences in the biological activities of the various geometric isomers of retinoids were first noted by George Wald, who ascertained the primary role in the visual process of all-trans-retinaldehyde (which Wald and co-workers originally termed "retinene"). In the eye, retinene is the photoproduct of 11-cis-retinaldehyde (which was originally termed "neo-b-retinene") when the latter is bound to visual pigment proteins such as rhodopsin [2]. When dissolved in organic solvents, these geometric isomers of retinaldehyde are distinct and chemically stable, meaning that under most conditions the all-trans form and 11-cis forms are not rapidly interconverted except when exposed to blue or ultraviolet light.

The all-trans- and 11-cis isomers of the corresponding acid (retinoic acid) are also stable and chemically distinct, as has been shown by their chromatographic separation from each other and from additional isomers such as: 7-cis; 9-cis; 13-cis; 9,13-dicis; and 11,13-dicis. As with retinaldehyde, these geometric isomers of retinoic acid can be interconverted upon absorption of ultraviolet light, and can subsequently be chromatographically separated from each other to yield the pure individual isomers. The separation methods, as well as the distinct spectroscopic properties of 9 of the resulting isomers of retinoic acid, are summarized in published work [12], which is incorporated herein by reference.

Only small amounts of purified 11-cis-retinoic acid have been prepared by photoisomerization and reversed-phase chromatography from other isomers. Other than this small-scale photochemical synthesis and purification, no stereospecific synthesis of 11-cis-retinoic acid has been reported. However, the all-trans, 9-cis, and 13-cis geometric isomers of retinoic acid have recently been prepared by oxidizing the corresponding retinoic acid isomers with sodium chlorite and resorcinol. This reaction was shown to proceed without loss of stereospecificity [Japan 4,253,934 1990]. Along with known stereospecific syntheses of 11-cis-retinaldehyde, summarized in [6] and [9], this points the way to a stereospecific synthesis of 11-cis-retinoic acid.

The all-trans isomer of retinoic acid has been given the trivial name tretinoin; the 13-cis isomer is known as isotretinoin. In this patent application, the 11-cis isomer of retinoic acid will frequently be abbreviated as "neotretinoin", in commemoration of George Wald's original neologism for 11-cis-retinaldehyde. For purposes of this application, therefore, neotretinoin therefore signifies the following chemical structure (which has a Registry Number of 124510-04-9):

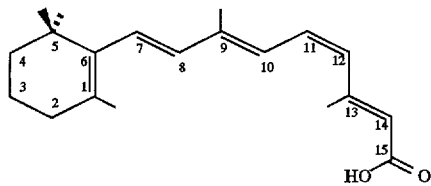

There is extensive history of the use of tretinoin for the treatment of dermatological conditions, including psoriasis and skin cancers [5]. This work established that topical treatment with tretinoin is of small benefit in treating psoriasis, inducing at best a partial remission. Topical treatment of skin with tretinoin is also known to cause irritation and peeling of the skin. This has led to the development of less irritating analogs of retinoic acid, such as: $C_{22}$ acid, which is simply tretinoin with a lengthened polyene chain [4,021,573 5/1977]; and α-hydroxy retinoic acid. [4,194,007 3/1980]. These analogs have been synthesized and described as the all-trans isomer only.

The generally mediocre results from treating psoriasis with tretinoin were greatly improved/upon with the introduction of the synthetic aromatic retinoid etretinate. Systemic treatment with etretinate produces significant melioration of psoriasis symptoms in a majority of patients. Systemic isotretinoin (13-cis-retinoic acid) is also useful for treating psoriasis. In a direct comparison with etretinate (which has only trans double bonds in its polyene side chain), oral isotretinoin is somewhat less efficacious as treatment for psoriasis, leading to moderate improvement in approximately 30% of patients [8]. Both systemic retinoids etretinate and isotretinoin-share a number of major side effects in a majority of patients who used them on a long-term basis, including dried epithelial tissues and hyperostosis [15]. When taken sytemically, they are also both teratogenic, making them ill-suited for use by women of childbearing age.

Both isotretinoin and etretinate have been shown to be more efficacious against psoriasis when administered in combination with ultraviolet light, either as psoralen in combination with UVA [11], or with UVB light alone [14]. However, it has apparently never been suggested that the synergistic effects of oral retinoid and ultraviolet light might be due to photoisomerization of the retinoid to a pharmacalogically more active geometric isomer (i.e., 11-cis).

Existing art includes the mention of the 11-cis isomer of retinaldehyde, along with a number of other retinal isomers, as possible therapeutic agents for dermatalogical conditions. In a previously-awarded, patent (U.S. Pat. No. 5,093,360), a total of 7 different geometric isomers of retinaldehyde and its derivatives, including the 11-cis isomer, were proposed by name as therapeutic agents for a wide variety of dermatological conditions, including psoriasis. However, none of the examples given in this patent actually involve the use of 11-cis isomer of retinaldehyde, so no activity distinct to it was noted. Furthermore, retinoic acid was not disclosed the '360 patent, only retinaldehyde and its associated hydrates, acetals, and hermiacetals:

U.S. Pat. No. 4,877,805 claims the use of retinoic acids and retinoic acid derivatives, and stereoisomers thereof, as treatment for sundamaged human skin. However, the 11-cis isomer is never specifically named in the claims or discussed in the description of the invention, so that no distinct effects of this specific isomer on the skin were noted or claimed. Furthermore, the use of retinoic acid as a treatment for conditions involving hyperproliferating cells (e.g. psoriasis) is never mentioned.

A PCT application by Kligman (9,315,740) claims the use of retinoic acid isomers, in combination with a corticosteroid, as a treatment for inflammatory dermatological conditions. These conditions include some that involve hyperproliferating cells (e.g. lichen planus), and the retinoids proposed include geometric isomers of retinoic acid. However, psoriasis is specifically excluded from the list of conditions for which this treatment is claimed to be useful. It would furthermore not be obvious to one skilled in the art that the use of 11-cis isomer of retinoic acid would result in efficacy against any of these conditions in the absence of the accompanying corticosteroid.

Likewise, a European patent (3,827,467) claims the use of combination therapy of retinoids with pyrimidine as a treatment for alopecia and other forms of hair loss. Alopecia is an occasional consequence of psoriasis. However, this treatment was not claimed to provide any general therapy for other aspects of psoriasis. Furthermore, the utility of the 11-cis isomer of retinoic acid was not specifically demonstrated, either in the absence or presence of the pyrimidine..

More recently, the retinoid BMY30047 (11-cis,13- cis-12-hydroxymethylretinoic acid δ-lactone), whose structure is shown below, was shown to be topically effective both in the reduction of utricles and the inhibition of ornithine decarboxylase in mouse skin [13]. It was proposed therefore that BMY30047 could be useful in treating psoriasis and other dermatological conditions. Furthermore, the in vivo activity was stereospecific for this particular isomer. In particular, isomerization of BMY30047 around the $C_{11}=C_{12}$ double bond led to reduced activity [21].

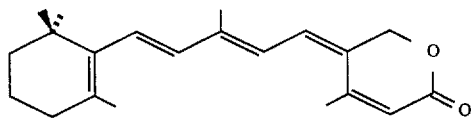

BMY30047

However, BMY30047 is chemically distinct from neotretinoin in a number of aspects, which a person skilled in the art would be likely to conclude are as important as the cis-trans isomeric state of the $C_{11}=C_{12}$ double bond for determining its biological activity. These unique structural features of BMY30047 include: (1) the presence of a second cis double bond (at $C_{13}=C_{14}$); (2) the presence oil a non-hydrogen substituent at $C_{12}$; (3) the absence of a free carboxylic acid (COOH) functionality; and (4) the presence of a closed-ring ester group (that is, a lactone). Furthermore, the relative spatial positions of the main chain and these other distinctive structural features of BMY30047 all change when the $C_{11}=C_{12}$ bond is isomerized. This could easily account for the stereochemical requirement at this bond for dermatological activity. In fact, the hydrolysis product of BMY30047 (11-cis,13-cis-12-hydroxymethylretinoic acid), which resembles neotretinoin even more than the parent compound, was found to have little or no activity in the utricle and ornithine decarboxylase assays. Therefore, from the results with BMY30047 it is not possible to discern that 11-cis-retinoic acid itself might also have some special utility in the treatment of dermatological conditions. In fact, the authors of published studies on this compound have never mentioned 11-cis-retinoic acid as being a related compound, although they did mention all-trans-retinoic acid.

BRIEF SUMMARY OF THE INVENTION

This invention consists of using 11-cis-retinoic acid as a treatment for psoriasis and other diseases involving hyperproliferation of cells. The essential novel teaching of this patent is that the 11-cis isomer of retinoic acid has a pharmaceutical activity that is distinct from that of the more widely known all-trans and 13-cis isomers. This activity manifests itself upon topical application as an ability to halt the hyperproliferative activity of the cells that give rise to psoriatic lesions, healing these lesions rapidly without adversely affecting the surrounding tissue.

The special activity of 11-cis-retinoic acid makes it necessary to synthesize this isomer stereoselectively, or else to separate it from other isomers, in order to obtain the maximum therapeutic effect from retinoic acid treatment. Furthermore, once the 11-cis isomer is separated from other isomers, it is crucial to keep its exposure to blue and ultraviolet components of the spectrum to a much lower level than is commonly necessary for pharmaceuticals, because of the rapid reverse photoisomerization that 11-cis-retinoic acid can undergo to form the less-active all-trans isomer. For example, approximately 1% of 11-cis retinoic acid is converted to the all-trans isomer per minute, when it is exposed to illumination having wavelengths between 340 and 380 nm and an intensity of one milliwatt per square centimeter. (This calculation is based on an approximate molar absorbance of 35,000 per cm in this wavelength range, and an approximate quantum yield of 0.1 for the photoisomerization of 11-cis to all-trans, which are based on published values.) Since ambient fluorescent lighting includes amounts of light in the near-UV wavelength range that are comparable to this amount, and substantial additional amounts of blue light that will also isomerize the neotretinoin, it is necessary to limit exposure to ambient lighting to several minutes at most.

The invention was developed as a result of experimentation by the inventor on his (my) own skin. I have been afflicted with an exfoliative guttate psoriasis, intermittently moderate to severe, since childhood. Extensive experimentation since 1979 with all-trans-retinoic acid (tretinoin) established that topical treatment with this compound was not effective in clearing my psoriasis, except whenever I exposed my tretinoin-treated skin to ultraviolet light (either natural sunlight or UV-B illumination from a sunlamp). Independently, professional dermatologists developed a combination therapy of oral isotretinoin with UV-B illumination, which proved to be efficacious against psoriasis. One explanation for the efficacy of such combination therapies has been that the retinoic acid serves as some kind of sensitizer for UV damage to nucleic acids in the cell, e.g. through the formation of a short-lived triplet state.

However, all along I suspected that a long-lived retinoic acid photoproduct, e.g. one of the lesser-known isomers of retinoic acid, was playing a direct role in inducing the cells to alter their proliferative pattern. Recently, a simple experiment has allowed me to test this hypothesis in a scientifically controlled fashion. That is, I have exposed a commercially-obtained retinoic acid gel to ultraviolet light prior to smearing it on psoriasis-affected areas of my skin, and have compared the results to those obtained at the same time with non-illuminated tretinoin gel on matched areas of skin. This experiment, which I have now repeated more than 10 times over 3 years on my own skin, gives a clear result. Illumination of tretinoin with ultraviolet light, even before it is applied to the skin, causes a striking increase in its ability to clear psoriasis lesions. Surprisingly, the pre-illuminated tretinoin seems to cause less irritation and erythema than the unilluminated tretinoin.

This treatment of psoriasis with pre-illuminated tretinoin is by itself a useful invention. It is clearly distinct from the current art of retinoid-UV combination therapy, in which UV light is applied to the patient's skin after the retinoid has been administered. The pre-illumination approach has a distinct advantage, in that it avoids the collateral effects of direct UV irradiation of the skin. By collateral effects, I mean those which are not mediated by retinoic acid photoreactions, and which therefore are not incurred upon treatment with pre-illuminated tretinoin. These collateral effects include pain, erythema, and tissue damage associated with sunburn, and probably the carcinogenicity effects of UV light as well. As topical tretinoin gels are already approved for sale, and UV light (in the form of natural sunlight or sunlamps) is also readily available, pre-illumination of tretinoin is a therapeutic approach that dermatologists can take advantage of immediately in treating psoriasis sufferers.

However, to make this invention more useful, it was necessary to determine which photoproduct of retinoic acid carries the anti-psoriasis activity. I have now established that it is the 11-cis isomer, which I call neotretinoin. This was done by preparing neotretinoin in an isomerically pure form, then testing it in comparison with the all-trans, 13-cis isomers, and 9-cis isomers. It was likely that the active photoproduct would be found among these isomers, since the 9-cis, 11-cis, and 13-cis isomers mentioned are known to comprise about 70% of the total photoproducts of tretinoin that are generated under conditions similar to those I use to prepare the pre-illuminated tretinoin gel [12].

The all-trans and 13-cis isomers needed for the comparison are available commercially, but not the 9-cis or 11-cis isomers. However, the 9-cis isomer is available as 9-cis-retinaldehyde, which I converted to 9-cis-retinoic acid by using a recently developed method [Japan 4,253,934 1990]. The 11-cis isomer is not available commercially, but I have prepared it in milligram quantities from 11-cis-retinaldehyde by adapting the same oxidation conditions used for the 9-cis isomer. At the current time, 11-cis-retinaldehyde is not commercially available, but it can be prepared in substantial quantities by using any of a number of published synthesis methods. To make the milligram quantities needed in the tests I have performed to date, it was adequate to photoisomerize commercially-available all-trans-retinaldehyde in acetonitrile, then to separate the resulting isomers by means of silica gel chromatography [6].

Despite requiring more steps, my novel approach to the synthesis of neotretinoin (preparing 11-cis-retinaldehyde, then oxidizing it) is currently preferable to photoisomerizing the retinoic acid and separating its isomers. This is because there are no conditions known which give as high a yield for photoisomerization of retinoic acid to the 11-cis isomer, as the >40% yield that is obtainable upon photoisomerization of retinaldehyde to the 11-cis isomer in polar solvents [12, 6]. Furthermore, 11-cis-retinaldehyde can easily be separated from other geometric isomers using silica gel chromatography, whereas the corresponding separation with retinoic acid is more difficult and requires expensive reverse-phase columns.

The novel approach I have taken to synthesizing the neotretinoin (11cis-retinoic acid) has allowed me to test the dermatological activity of this substance directly on my own skin, after mixing it into a non-irritating cream at a concentration of 0.001%. (This is also approximately the concentration of neotretinoin that is produced by irradiating commercially-available 0.01% tretinoin gel.) A direct comparison against the 3 other cited isomers, constituted at the same concentration and applied at the same time and in the same quantity as the 11-cis isomer but on different areas of psoriasis-affected skin, has repeatedly given an unequivocal result. Upon a single application, only the 11-cis isomer shows substantial clearing of psoriasis lesions, starting about 36 hours after application and continuing over the next several days. The amount of erythema and irritation experienced during this period is greatly reduced for all 3 of the cis isomers, compared with that produced by the all-trans isomer. Repeated application of the neotretinoin cream over the space of a week leads to complete healing of the psoriatic lesions in the area of skin treated. This is qualitatively different from what is observed in the areas of skin treated in parallel with the other 3 isomers, which produce at best a slight temporary decrease in the scaling and itching, while still leaving a reddened patch at the site of each psoriasis lesion. The topical neotretinoin thus exhibits an effect that is distinct from any of the other isomers.

I also expect, based on theoretical grounds, that the neotretinoin will also be useful against other diseases involving hyperproliferation and improper differentiation of cells. In the skin, retinoic acid seems to be operating as an "ultraviolet dosimeter." That is, the isomerization of all-trans-retinoic acid, a normal component of human skin, to its 11-cis isomer, signals to the skin cells that they should stop dividing and undergo terminal differentiation. In skin, this leads to exfoliation of the dead keratinocytes. It is desirable for this process to occur more quickly when skin is exposed to ultraviolet light, because of the likelihood that the ultraviolet light will cause DNA damage that could lead to skin cancer. By triggering the terminal differentiation of those cells that get the highest UV dosage, the retinoic acid photoisomerization process could protect the skin from solar carcinogenesis. Indeed when normal untreated skin is exposed to enough ultraviolet light to cause a mild sunburn, there is a peeling reaction that is very similar to that seen with the pre-illuminated tretinoin even in the absence of direct illumination on the skin. The time course of the peeling in both cases is similar, suggesting that the normal peeling reaction following sunburn may be mediated, at least in part, by retinoic acid photoisomerization to one or more of its cis isomers.

It seems likely that simultaneous production of more than one cis isomer may be necessary to mediate this ultraviolet dosimeter effect, since the isomerically pure 11-cis-retinoic acid elicits only a very mild peeling reaction that mimics post-sunburn peeling more weakly than the peeling produced by the mixed UV-isomerate of tretinoin. However, it seems that the 11-cis isomer is the most important in producing the peeling effect, since individually none of the other isomers produces as much peeling as the 11-cis isomer. It makes sense that nature would select the 11-cis isomer as the one to trigger the ultraviolet dosimeter signal, since in polar solvents this is generally the isomer which has the highest rate of formation in the light, relative to its thermal rate of formation in the dark [12]. That is, starting with the all-trans-retinoic acid, only the 13-cis isomer has a slightly higher photochemical rate of formation than 11-cis, but it is preferable to use the 11-cis isomer as a signaling molecule because it has a very low rate of thermal formation in the dark due to its sterically-hindered structure. The 13-cis isomer, on the other hand, is almost as stable as the all-trans starting material, and it would be expected to form at a fairly rapid rate at body temperature even in the dark. Use of the 11-cis isomer as a signal for accumulated UV dosage thus provides the highest sensitivity.

This ultraviolet dosimeter theory for retinoic acid activity helps to explain the known action spectrum of psoriasis phototherapy, which reaches a maximum near 320 nm and declines to near 0 below 290 nm [4]. This is above the wavelength of the longest-wavelength absorption band of DNA and RNA at 260 nm, as well as the longest-wavelength protein absorption band at 280 nm. This suggests that psoriasis phototherapy does not function via direct photo-reaction of nucleic acids or of proteins. Instead, it is more likely mediated by some species that absorbs maximally above 300 nm. I propose that this species is retinoic acid, and that psoriasis monotherapy by UV light is mediated principally by photochemical formation of neotretinoin in the skin. Retinoic acid itself has an absorption maximum near 360 nm, but under normal conditions in the skin (around 5 nanomolar and pH 7), most retinoic acid probably exists as retinoate anion [18]. Retinoate absorbs at shorter wavelengths than retinoic acid, with an absorption maximum near 340 nm and a bandwidth (half-height at half maximum) of 20 nm. I hypothesize that the small discrepancy between the retinoate absorption maximum and the observed maximum of 320 nm for the phototherapy action spectrum might result from factors such as a wavelength-dependent quantum yield for all-trans to 11-cis photoisomerization, or the filtering out of light with wavelengths near 340 nm by other light-absorbing materials in the skin (such as melanin).

There are important new evolutionary implications suggested by the ultraviolet dosimeter function of retinoic acid. This function is clearly intermediate between the two other known functions of retinoids in multicellular organisms: sensing of visible light, and control of cellular differentiation. The former is known to be mediated by a family of G-protein-coupled membrane receptors (the visual pigments), while the latter has been thought to be mediated exclusively by nuclear receptors related to the hormone-binding receptors. However, searches for nuclear receptors that bind retinoic acid have so far turned up only the RAR and RXR families of receptors, which bind predominantly the all-trans and 9-cis isomers of retinoic acid [19]. Neither of these receptors has an affinity for 11-cis-retinoic acid sufficiently high to mediate a psoriasis phototherapeutic effect that is hypothetically initiated by conversion of endogenous tretinoin to neotretinoin. The maximal concentration of neo-retinoin that could be produced by photoisomerization of endogenous 5-nM tretinoin is probably less than 1 nM, which is considerably less than the dissociation constant of the RAR and RXR receptors for this isomer of retinoic acid. Despite great efforts to dissect the function of RAR and RXR receptors in skin development, these nuclear receptors do not adequately explain the myriad functions of retinoids in mammalian skin since transgenic mice with both types of receptors knocked out seem to develop fairly normal skin [22].

I therefore strongly suspect that the neotretinoin is acting via an undiscovered receptor distinct from RAR and RXR. This is probably the reason why widespread knowledge and intensive experimentation on the latter 2 receptors has not led anyone else to the realization that neotretinoin has a useful therapeutic effect for dermatological diseases. The undiscovered neotretinoin receptor could be a nuclear receptor related to but distinct from RAR and RXR, but there is compelling evolutionary reason to believe that it could also be a G-protein-coupled membrane receptor. While both light-sensing and differentiation-inducing function of retinoids are present in most phyla of multicellular animals, the light-sensing function seems to be more ancient because it extends back to unicellular organisms (e.g. Chlamydomonas). Furthermore, not only are all known light-sensing functions of retinoids mediated by G-protein-coupled receptors, such receptors are also involved in many differentiation-inducing processes. Thus, it seems likely that an activity that is intermediate between these two (ultraviolet dosimetry as a trigger for terminal differentiation or apoptosis) could well have served as an evolutionary stepping-stone between the two principal types of retinoid-mediated processes. This would suggest that it could well be mediated by either, or perhaps both, types of receptor: nuclear or membrane-bound.

It is even plausible that ultraviolet dosimetry by retinoic acid could have been one of the most primordial signals for cellular differentiation. In fact, development of an ultraviolet-light-triggered signal for differentiation and/or apoptosis would probably have been crucial to the early evolution of multicellular animals near the surface of the earth's waters. This would necessarily have been the optimal location of foodstuffs (i.e. autotrophs using sunlight for photosynthesis), yet swimming in these surface waters would have exposed the cooperating multicellular proto-animals to the most dangerous DNA-destroying agent in the biosphere at that time: ultraviolet light. In order for these loosely-cooperating cells with a shared genetic heritage to pass on an intact genome to their progeny, the best strategy would have been for the cells to develop a program that instructed those with a significant UV dosage to cease dividing, lest they should undergo a mutation that would render them incapable of continuing the mutually-beneficial cooperation.

The foregoing is of course a very speculative hypothesis, but it suggests that many cell types besides skin cells might have programmed into them a receptor for neotretinoin. The fact that retinoids are known to have various types of cancer-preventitive and antineoplastic activity, that are not fully ascribable to RAR- and RXR-mediated processes, leads obviously to the possibility that the anti-neoplastic and cancer-preventive effects of retinoids could be mediated largely by neotretinoin and its as yet-unknown receptor(s). This is a powerful hypothesis, since it could explain the decreased incidence of the most common cancers, including those of lung, breast, and colon, as well as melanoma, among people living in latitudes closer to the equator [17]. This epidemiological result could have an explanation as simple as the greater amount of neotretinoin that these sun-exposed people are constantly making in their skin and diffusing around to their other tissues.

Given not only the foregoing speculation, but also the hard experimental facts (1) that other retinoids and β-carotene have been found to have anti-neoplastic and cancer-preventive activities and (2) that neotretinoin has now been shown to carry a special differentiation-inducing activity in hyperproliferating cells, an obvious application of neotretinoin will be in treating and preventing cellular hyperproliferation in both benign and malignant neoplasms. This is especially true for those cancers—such as lung, bowel, and breast cancer—that are known from epidemiological studies to prevail (like psoriasis) at high latitudes.

EXPERIMENTAL EXAMPLE

Experiment #1

Preparation of 11-cis-retinoic acid from commercially available all-trans-retinal.

The latter starting material (20 mg) was dissolved at a concentration of 4 mg/mL in dry acetonitrile in a clear glass tube. This tube was purged with $N_2$ and tightly stoppered, then exposed while stirring to the light from a 50-cm-long fluorescent lamp (30W, 680 lux) at a distance of 15 cm for 60 min. This period of exposure assumes a maximum of 1 cm path length of the light through the retinal solution; for longer path length or more concentrated solutions the exposure time must be lengthened proportionally.

The material was then taken out of the light and was kept in the dark or under dim red light (except for brief periods in room light, totaling no more than 1 min) for all subsequent operations. Silica gel (0.5 g, 28–200 mesh, 22 Å average pore diameter) was added, then acetonitrile solvent was evaporated under vacuum centrifugation. The retinal isomerate, adsorbed to the silica gel, was taken up in petroleum ether (several aliquots totaling 5 cm), and applied on top of a 1-cm-dia. glass column packed with the same silica gel in petroleum ether. The column was then developed with 10% diethyl ether in petroleum ether, both of which were well-purged with nitrogen prior to mixing, and subsequently kept away from air. Fractions of 0.5 mL were collected. Retinal content of the fractions was quantitated by their 380-nm absorption. Four peaks were resolved by the column, which were assigned in order of elution as the 13-cis, 11-cis, 9-cis, and all-trans isomers, using previously published information [3]. The second peak, corresponding to the 11-cis isomer, was largest, and accounted for approximately 30% mg of the 380-nm absorbance of the starting material.

This method is acceptable for separating small quantities of 11-cis-retinal in the absence of expensive chromatography equipment. In a preferred embodiment of the invention, however, the open column chromatography would best be replaced by preparative high-performance liquid chromatography (HPLC). For larger quantities, it would be better to use centrifugal partition chromatography, as described in a note in the *Journal of Chromatography*, 357:340–343 (1986) by Bruening and co-workers.

To oxidize 11-cis-retinal selectively to 11-cis-retinoic acid, the petroleum ether was removed from the 11-cis-retinal, which was then dissolved in 0.1 mL of reagent-grade tert-amyl-alcohol in a test tube. This tube was chilled on ice, then to it were added sequentially: 0.01 mL of a 25% solution of resorcinol in tert-amyl-alcohol; 0.02 mL of 40% sodium dihydrogen phosphate in water; and 0.02 mL of 25% sodium chlorite in water. (These are all weight percentages.) The tube was warmed to room temperature, and the aqueous and organic phases were mixed vigorously by vortexing. The reaction mixture was kept at room temperature for 45 min, with intermittent vortexing to keep the phases well mixed. Then 0.2 mL water was added, the reaction tube was centrifuged at 1500 rpm to aid in separating the phases, and the lower (aqueous) phase was removed. The extraction with water was repeated twice more to remove the oxidants (sodium chlorite and resorcinol). Then, after adding 0.2 g silica gel, the tert-amyl-alcohol was removed under vacuum centrifugation. The silica-adsorbed reaction product was suspended in petroleum ether, transferred to the top of a 100-cm-long silica gel column as described above, and eluted with 20% diethyl ether in petroleum ether as described above. The retention time for the neotretinoin (11-cis-retinoic acid) was substantially greater than that of the unreacted 11-cis-retinaldehyde, making it easy to separate them. After elution of the neotretinoin band, the organic solvent was removed by evaporation, and the neotretinoin was taken up in 100% ethanol, denatured The total yield of neotretinoin, based on its 360 nm absorbance, was 2 mg (approximately 30% of the 11-cis-retinaldehyde starting material).

The identity and purity of the neotretinoin was confirmed with reverse-phase thin-layer chromatography (RPTLC). Six samples were spotted onto a single RPTLC plate: an aliquot of the neotretinoin recovered from the column and kept in the dark; an identical aliquot of the neotretinoin preparation that had been exposed 3 hours to a 30-W fluorescent white light as described above; and similar-sized aliquots of authentic tretinoin (all-trans-retinoic acid) and isotretinoin (13-cis retinoic acid) solutions that had either been kept in the dark, or illuminated along with the neotretinoin. The TLC plate was developed using acetonitrile:methanol:isopropanol:water (30:25:15:30). All 3 of the illuminated samples gave essentially identical RPTLC patterns, showing 6 distinguishable yellow spots. Two of these (the second-fastest and the slowest, respectively) corresponded to the positions of the authentic unilluminated 13-cis and all-trans isomers, as expected from previously published HPLC results [12]. The third-fastest spot migrated at the same rate as the main spot observed for the neotretinoin preparation, again as predicted by the published reverse-phase HPLC results. The neotretinoin showed only very faint contaminant spots, indicating it was predominantly the desired 11-cis isomer.

Experiment #2

Treatment of psoriasis with pre-illuminated tretinoin.

A tretinoin gel of 0.01% concentration (Retin-A gel, Ortho Pharmaceuticals) was used as the starting material because it is commercially available to the public and is suitable for pharmaceutical use. The gel was preferred to the cream because of greater transparency to light. To illuminate the gel uniformly, 50 g (2 oz) of it was placed between two 10-inch-square sheets of Saran food wrap, which were then rolled with a rolling pin to spread the gel to a I-turn-thick-disc covering a roughly circular area with a 9-inch radius. The edges of the two pieces of plastic wrap were clamped together around almost the entire circumference, using a 10" embroidery clamp ring, in order to prevent loss of volatile solvent during the illumination. Then this sample was taken outdoors and illuminated for 30 min by midday sunlight, or was placed 8 inches away from a mercury-vapor sunlamp (Sperti) for 10 minutes. The exposure time and other conditions were selected to maximize the formation of the 11-cis photoproduct, and to limit the formation of dicis compounds, by extrapolating from the time-dependence of isomer formation that was published previously [12]. After the illumination was over, the tretinoin gel was collected and mixed in equal parts with a non-irritating skin moisturizing cream containing petroleum, water, mineral oil, and propylene glycol. The ethanol in the gel was allowed to evaporate, then the resulting cream was sealed in an air-tight, light-tight container. A control sample of un-illuminated tretinoin cream was prepared by executing the same steps, including the rolling between two pieces of plastic food wrap, except that the tretinoin gel was kept away from light to prevent its photoisomerization.

The pre-irradiated tretinoin, and the control, were spread lightly every third day for 2 weeks over matched areas of psoriasis-affected skin, e.g. on opposite legs. The effects were monitored carefully, while the treated areas were kept covered with clothes to avoid photoisomerization of the applied tretinoin by ambient light. Within 36 hours after the first treatment, there was a marked difference in the appearance of the psoriasis lesions treated with the two different creams. In the area treated with the pre-illuminate cream, the scaly covering of the lesions was replaced increasingly wispy flakes. Within 48 hours, this exfoliating dead tissue resembled the epidermal peeling that occurs in normal skin following a mild sunburn. A mild post-sunburn-like peeling was also initiated in the areas of normal skin surrounding the psoriasis lesions.

In the areas treated with un-illuminated tretinoin, on the other hand, there was increasing erythema, accompanied by a sensation of stinging and tightness of the skin, that affected the psoriasis lesions as well as of the surrounding tissue. The flaking scale on the lesions was replaced by a harder, crust-like surface that somewhat resembled the scar tissue that appears when a scab first falls off a healed abrasion.

These differences between the effects of pre-illuminated and un-illuminated tretinoin deepened with continued treatment. Within a week, the areas treated with the pre-illuminated tretinoin were largely free of obvious psoriasis lesions, although upon close inspection some of the sites of the former lesions were still a bit different from the surrounding normal skin. There was generally a small amount of irritation and erythema experienced in these normal-skin areas, and continued mild exfoliation or peeling.

The areas treated with un-illuminated tretinoin, however, still had obvious red spots and scar- or welt-like tissue at the original sites of psoriasis lesions, as well as a general erythema in surrounding areas. Furthermore, the skin felt painfully tight, and tender when touched.

This experiment gave similar results when carried out on different areas of the body, including my legs and knees; my arms; my torso; my eyebrows; and my ears. The proilluminated tretinoin was also found to alleviate psoriasis symptoms when applied to the scalp, but this was not done in a controlled fashion.

Experiment #3

Comparative treatment of psoriatis with 4 different retinoic acid isomers.

A non-irritating moisturizing cream containing water, petrolatum, mineral oil, and propylene glycol (CVS moisturizing cream) was used as a vehicle to deliver 0.001% retinoic acid, as each of 4 different geometric isomers, to matched psoriasis-affected areas on my skin. The isomers used were all-trans (obtained in crystalline form from Sigma Chemical Company); 13-cis (obtained from the same commercial source); 11-cis (prepared as described above under Experiment #1); and 9-cis, prepared by oxidizing commercially-obtained 9-cis-retinaldehyde by using the same procedure described in Experiment #1 for the 11-cis isomer. Roughly equal concentrations of the #our isomers were obtained by making ethanolic solutions with matched absorbances of approximately 1.0 at 360-nm, then adding equal amounts of these 4 solutions to 4 different aliquots of the moisturizing cream, then mixing them in the dark while allowing the ethanol to evaporate. The 4 creams were stored in separate light-tight, air-tight containers. Approximately 2 g of each cream was spread across the particular area of skin assigned to it, every third day for 2 weeks. Four different latex gloves were used to spread the 4 creams, in order to avoid cross-contamination of the isomers, and exposure of the treated areas to light (especially ultraviolet light) was carefully avoided.

The results with the all-trans (tretinoin) cream were generally similar to those described for the control ("unilluminated") tretinoin-treated areas in Experiment #2 above. The amount of erythema and irritation was a bit reduced, due to the lower dosage level applied. With all 3 of the cis isomers, on the other hand, the erythema and irritation were minimal or unnoticeable.

In the area treated with the 11-cis isomer (neotretinoin), the psoriasis lesions began to heal within approximately 48 hours after the first treatment. The amount of skin peeling, both at the site of the psoriasis lesion and in the surrounding normal skin, was significantly reduced compared with that obtained using proilluminated tretinoin (see Experiment #2), while the healing was as fast or faster. Obvious peeling was generally confined to the circumference of the lesions. The lesions remained perceptible only for about the first week of treatment, and within 2 weeks the area treated with the neotretinoin cream was lesion-free and completely normal in appearance. The skin in this area remained free of lesions for several weeks thereafter, without the application of any maintenance therapy.

In the areas treated with similar dosages 9- and 13-cis isomers, on the other hand, there was only very minor improvement. For example, the psoriasis lesions became softer and less scaly, and they took on the appearance of small red first-degree burns. However, they aid not disappear, and they returned to their pre-treatment appearance within several days after the end of the two-week therapy period.

The therapy has so far been tried only on a single patient, due to the small quantities of neotretinoin available as well as the difficulty of treating other humans prior to public disclosure of the invention. However, even these few controlled experiments have directly demonstrated that utility of the 11-cis isomer of retinoic acid as a treatment for psoriasis, a skin disease caused by hyperproliferation and incomplete (or improper) differentiation of keratinocytes. These experiments also clearly point the way to using the same neotretinoin as a treatment for other diseases involving cells that are hyperproliferating and improperly differentiated.

ADDITIONAL COMMENTS

While the preferred embodiment is described above, my invention encompasses considerable variation in the composition of the neotretinoin-based pharmaceutical, in the means of delivery to a site of hyperproliferating cells, and in the type of cells involved. For example, in treating the hyperproliferating keratinocytes in psoriasis, the exact concentration of the neotretinoin, and the composition of the inactive ingredients in the vehicle used to spread it, are unlikely to be of major importance, as long as this vehicle is non-irritating and capable of dispersing the neotretinoin over and somewhat into the skin surface. Furthermore, a systemic mode of delivery is also likely to be useful in some cases, such as treatment of hyperproliferating cells involved in neoplastic tissues in internal sites within the body.

What is claimed is:

1. The method of preparing retinoic acid having improved efficacy for topical treatment of the skin condition psoriasis, and having reduced irritancy to human skin, comprising the steps of:

a. synthesizing retinoic acid, wherein said retinoic acid consists of a mixture of isomers, b. converting at least one non-11-cis-retinoic isomer to 11-cis-retinoic acid to increase the concentration level of 11-cis-retinoic acid to a weight concentration of at least 10% of the total weight of retinoic acid and c. applying directly to psoriasis involved areas of the body skin having said psoriasis skin condition, said 11-cisretinoic acid being in a weight concentration range of 0.0001%–10% of the total composition and the remainder being an acceptable topical vehicle which is non-irritating to skin.

2. The method of claim 1, wherein said vehicle comprises at least one member from the group consisting of water, mineral oil, petrolatum, propylene glycol, glycerin and mixtures thereof.

3. The method of claim 1, wherein said step of increasing the concentration of the 11-cis isomer comprises the step of ultraviolet illumination of at least one non-11-cis isomer of retinoic acid.

4. The method of claim 1, further comprising the step of ultraviolet or visible illumination of a member from the group consisting of retinaldehyde and retinol, thereby forming as a reaction product, 11-cis-retinaldehyde, or 11-cis-retinol, and oxidizing said reaction product to form 11-cis-retinoic acid.

5. The method of claim 4, wherein said oxidizing of said reaction product comprises contacting said reaction product with a chlorite salt and resorcinol as oxidizing agents.

6. The method of claim 4, wherein said vehicle includes at least one member selected from the group consisting of water, petrolatum, mineral oil, glycerin, and mixtures thereof.

7. The method of claim 4 wherein said vehicle also includes other isomers of retinoic acid, said other isomers not to exceed 90% of the total concentration of retinoic acid, on a weight basis.

8. The method of claim 4 wherein said 11-cis-retinoic acid is the photo reaction product of the ultraviolet illumination of a second geometric isomer of retinoic acid, said second geometric isomer of retinoic acid differing from said 11-cis-retinoic acid only in the cis-trans isomer state of at least one of its four non-ring C=C double bonds.

9. The method of claim 8 wherein the said second isomer of retinoic acid is one of the following: all-trans; 7-cis; 9-cis; 13-cis; 7,9-dicis; 7,11-dicis; 9,11-dicis; 9,13-dicis; or 11,13-dicis.

10. A composition of matter consisting essentially of 11-cis-retinoic acid in a weight concentration range of 0.0001%–10% of the total composition and the remainder being a substance which is non-irritating to skin, the weight of 11cis-retinoic being at least 10% of the combined weight of all other cis-trans isomers of retinoic acid in the composition.

11. A composition of claim 10, wherein said substance is an inert substance, non-irritating to human skin, said inert substance being water in a concentration range of 31%–99% of the total composition.

12. A composition of claim 10, wherein at least a portion of said substance is an inert substance, non-irritating to human skin, said inert substance being a member of the group consisting essentially of water, petrolatum, mineral oil, glycerin, and propylene glycol and mixtures thereof.

13. The composition of matter of claim 10, wherein said composition is a cream comprising a mixture of petrolatum, mineral oil, glycerin, and water.

14. The composition of matter of claim 10, wherein said composition is for use in the treatment of psoriasis, said concentration range being from about 0.001% to 10% of said total composition.

* * * * *